United States Patent
Sugar et al.

(10) Patent No.: US 11,856,921 B1
(45) Date of Patent: Jan. 2, 2024

(54) THERAPEUTIC PAD WEARABLE BY ANIMALS

(71) Applicants: Brenda Sugar, Bennett, CO (US); Deborah Clifford, Bennet, CO (US)

(72) Inventors: Brenda Sugar, Bennett, CO (US); Deborah Clifford, Bennet, CO (US)

( * ) Notice: Subject to any disclaimer, the term of this patent is extended or adjusted under 35 U.S.C. 154(b) by 1483 days.

(21) Appl. No.: 16/158,821

(22) Filed: Oct. 12, 2018

(51) Int. Cl.
- *A61F 7/10* (2006.01)
- *A01K 13/00* (2006.01)
- *A61F 7/02* (2006.01)

(52) U.S. Cl.
CPC .... *A01K 13/006* (2013.01); *A61F 2007/0225* (2013.01); *A61F 2007/108* (2013.01)

(58) Field of Classification Search
CPC ........... A01K 13/006; A61F 2007/0225; A61F 2007/108
See application file for complete search history.

(56) References Cited

U.S. PATENT DOCUMENTS

| | | | |
|---|---|---|---|
| 234,247 A | 11/1880 | Classen | |
| 288,949 A | 11/1883 | Ludeke | |
| 5,928,275 A * | 7/1999 | Yates | A61F 7/034 607/108 |
| 5,996,537 A * | 12/1999 | Caditz | A01K 13/008 54/79.1 |
| 7,325,516 B2 * | 2/2008 | Moore | A01K 27/002 119/725 |
| 2007/0255187 A1* | 11/2007 | Branch | A61H 23/02 601/15 |
| 2014/0358205 A1* | 12/2014 | Robke | A61F 7/10 607/108 |
| 2015/0327969 A1* | 11/2015 | Entler | A61F 7/08 602/79 |
| 2019/0223409 A1* | 7/2019 | Godfrey | A61F 7/08 |

* cited by examiner

*Primary Examiner* — Kaitlyn E Smith
*Assistant Examiner* — Yasamin Ekrami
(74) *Attorney, Agent, or Firm* — SANCHELIMA & ASSOCIATES, P.A.; Christian Sanchelima; Jesus Sanchelima

(57) ABSTRACT

The present invention is a therapeutic pad that is wearable by an animal to provide treatment for injury or pain without hampering mobility. Therapeutic pad includes a jacket/wrap, a pocket and at least one of a heating pack and/or a cooling pack. Jacket is made of flexible material, wearable by animal and made of various shapes to fit on different body parts of animal Jacket/wrap can be provided with fasteners that can easy wearing of jacket/wrap by animal Pocket can be provided anywhere on jacket/wrap and can be permanently or temporarily connected with jacket/wrap or can be an integral cavity of jacket/wrap. Heating pack and/or a cooling pack is provided within pocket. Heating pack and/or a cooling pack provides therapeutic treatment on affected area(s) for reducing swelling and/or pain.

1 Claim, 3 Drawing Sheets

THERAPEUTIC PAD WEARABLE BY ANIMALS

II. BACKGROUND OF THE INVENTION

1. Field of the Invention

The present disclosure relates to a therapeutic pad for animals that provides treatment to injury or pain. More particularly, the present disclosure relates to a therapeutic pad to be wrapped on animal's body to provide treatment for injury or pain without hampering animal's mobility.

2. Description of the Related Art

When an animal is injured or is in pain because of a wound, muscle tissues of animal is required to be treated either by heat therapy or cold therapy to prevent swelling and reduce pain. However, for treatment, animal is required to remain at one position for a considerable period of time. As it is difficult for animal to remain at one position for a considerable period of time, there is a requirement for therapeutic pad for animals that facilitates therapeutic treatment without hampering mobility of animal.

Several designs for various pet pads have been designed in the past. None of them, however, includes a therapeutic pad that is wearable by an animal to provide treatment for injury or pain without hampering their mobility.

Applicant believes that a related reference corresponds to US patent application 20120234247 filed by Radio Systems Corp for an energy efficient heating pet pad. The Radio Systems Corp reference discloses a contoured and heated pet pad which is structured for energy efficiency, warmth, and comfort for the pet, and which is capable of being conveniently fit into dog houses or other designated pet areas without having significant amounts of wasted space. However, the pet is to be positioned on pet pad thus restricting pet's mobility.

Another related application is US patent application number 20060288949 filed by Hyperion Innovations Inc. for a portable heated padding for pets. The portable heated bedding apparatus for pets is provided with a cushion material sized for accommodating a pet animal. However, the pet is to be positioned on pet pad thus restricting pet's mobility.

Other documents describing the closest subject matter provide for a number of more or less complicated features that fail to solve the problem in an efficient and economical way. None of these patents suggest the novel features of the present invention.

III. SUMMARY OF THE INVENTION

It is an object of the present invention to provide a therapeutic pad that is wearable by an animal to provide treatment for injury or pain without hampering their mobility.

It is an object of the present invention to provide a therapeutic pad that includes a jacket/wrap wearable by an animal and the jacket/wrap is defined with a pocket to hold a heating pack and/or a cooling pack for providing therapeutic treatment on affected area(s) for reducing swelling and/or pain.

It is an object of the present invention to provide a therapeutic pad for animals that includes a jacket/wrap with fasteners that facilitates easy wearing of jacket/wrap.

It is an object of the present invention to provide a therapeutic pad for animals that is wearable to prevent animals from licking of wounds without usage of cone of shame that causes discomfort.

Further objects of the invention will be brought out in the following part of the specification, wherein detailed description is for the purpose of fully disclosing the invention without placing any limitations thereon.

IV. BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents an isometric view of a U-shaped therapeutic pad 10a in a working environment worn on a body portion 05a of an animal 05.

Figure 4:
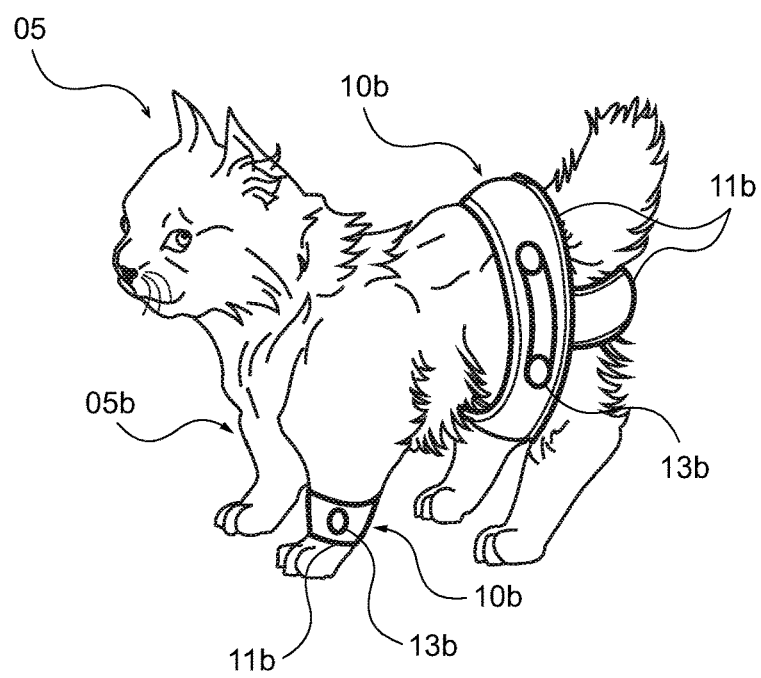

FIG. 4 represents an isometric view of a cylindrical-shaped therapeutic pad 10b in a working environment worn on a leg portion 05b and a back portion of an animal 05.

Figure 5:
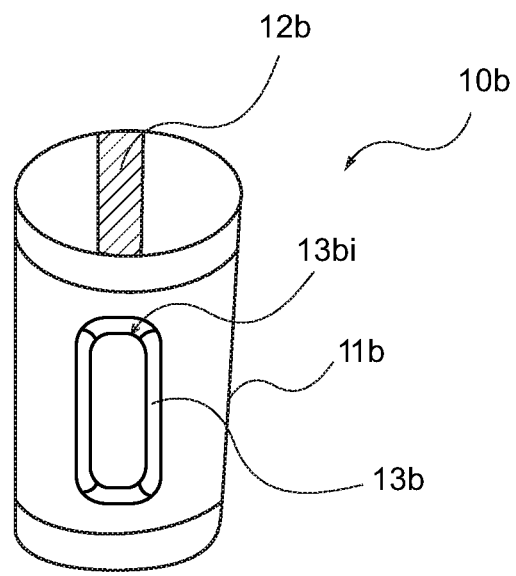

FIG. 5 shows an isometric view of cylindrical-shaped therapeutic pad 10b in a closed configuration.

Figure 6:
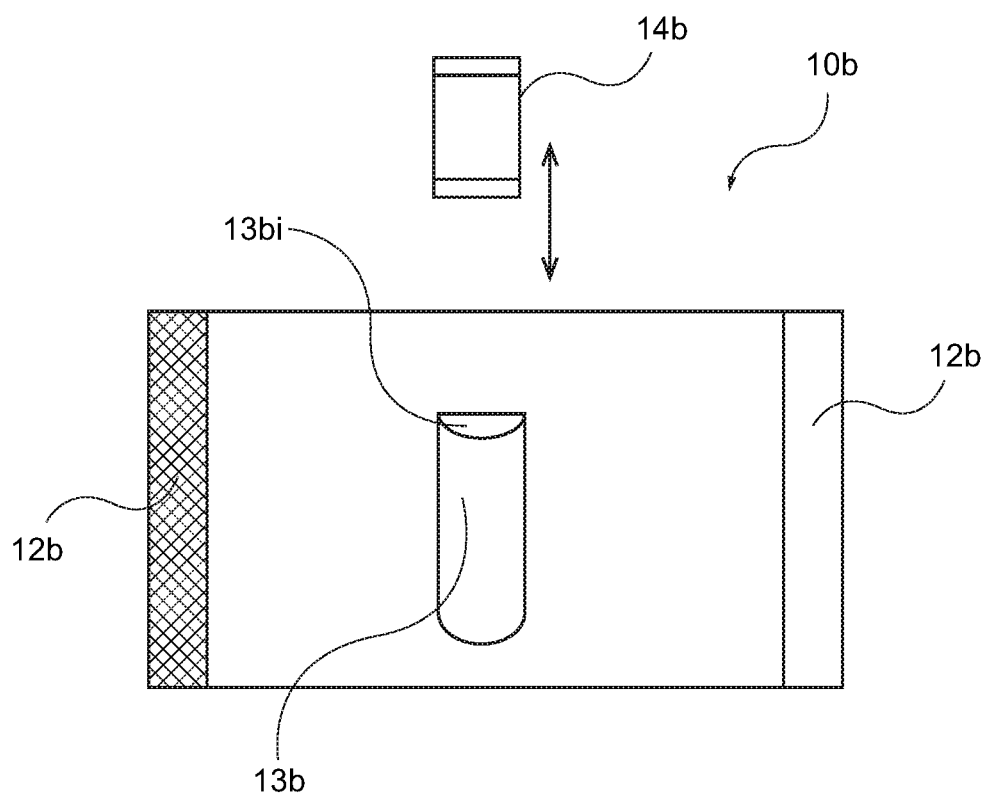

FIG. 6 shows a schematic representation of cylindrical-shaped therapeutic pad 10b in an open configuration.

V. DETAILED DESCRIPTION OF THE EMBODIMENTS OF THE INVENTION

Figure 1:
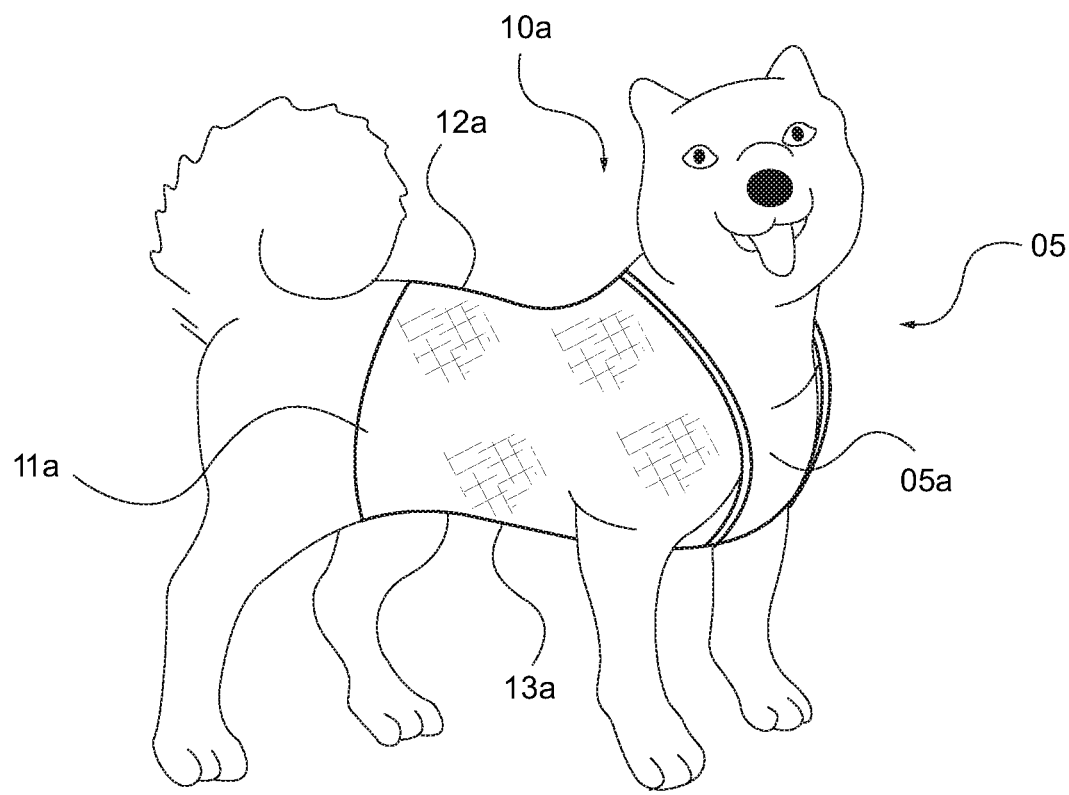
Figure 2:
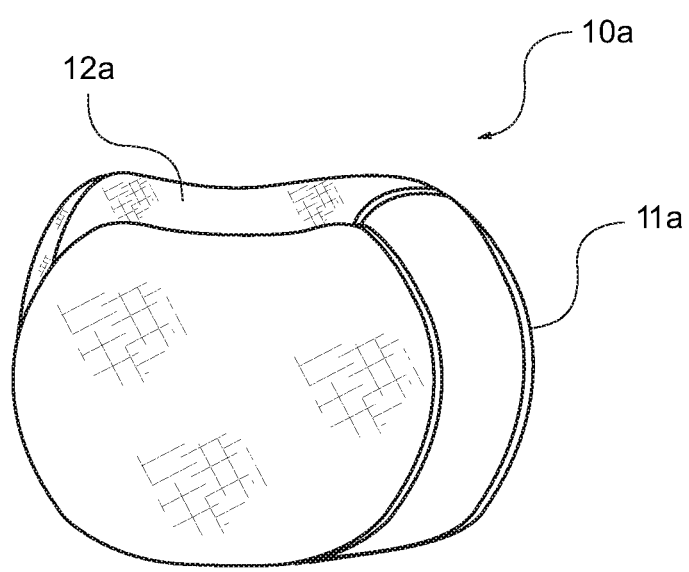
FIG. 2 shows an isometric view of U-shaped therapeutic pad 10a in a closed configuration.
Figure 3:
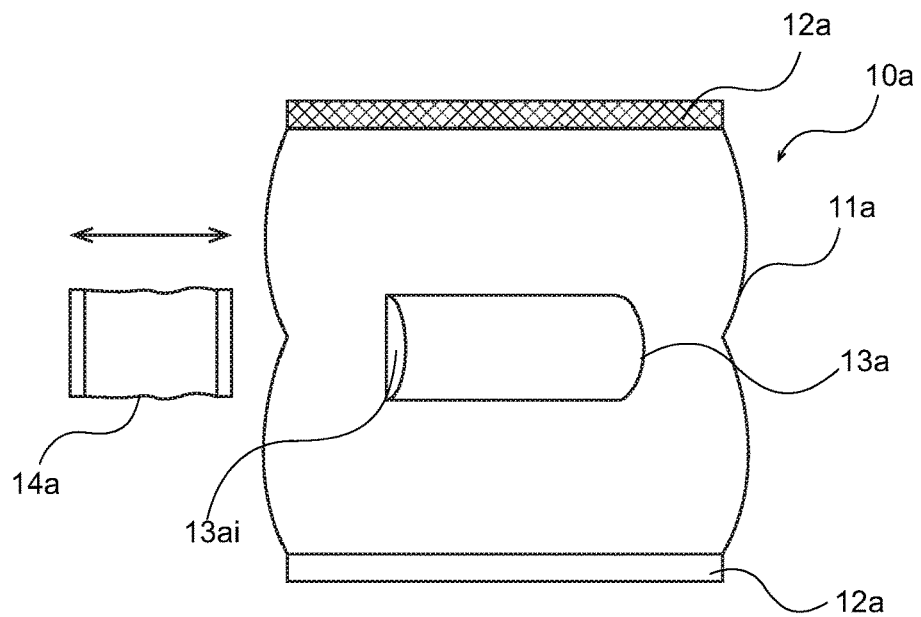
FIG. 3 shows a schematic representation of U-shaped therapeutic pad 10a in an open configuration.

Referring now to the drawings, FIGS. 1-3, where the present invention is generally referred to with numeral 10a, it can be observed that a U-shaped therapeutic pad, in accordance with one embodiment, is provided that includes a jacket/wrap 11a, at least one fastener 12a, a pocket 13a and at least one of a heating pack and/or a cooling pack 14a.

Jacket/wrap 11a is wearable on a body portion 05a of an animal 05 such as a dog as illustrated in FIG. 1. Jacket/wrap 11a can be typically of a material flexible enough to take the shape of the body portion 05a of animal 05. In one embodiment, jacket/wrap 11a can be made of stretchable material that can be stretched enough to be worn by animal 05 without use of any fasteners. Material of jacket/wrap 11a or an outer layer of jacket/wrap 11a can be selected such that the animal 05 is detoured from liking or chewing the wound on which jacket/wrap is worn or wrapped, thus preventing the need to use the cone of shame.

In another one embodiment, jacket/wrap 11a is provided with fastener 12a. In the depicted embodiment, fastener 12a is Velcro. In another embodiment, fastener 12a can be a zip or press-buttons. Although the present disclosure is described with fasteners 12a such as Velcro, zip or press-buttons, however, the present disclosure is not limited to the once as described and illustrated and any other fastener(s) that can easily manipulate jacket/wrap 11a between an open configuration and a closed configuration. Typically, jacket/wrap 11a can be of a nylon material or any other type of polymeric material or cotton based material that cannot be chewed by animal Jacket/wrap 11a is adjustable such that it can be worn or wrapped on different body parts of animal 05 such as jacket/wrap 11a can be worn on abdominal body portion as well as adjusted to be worn on back body portion by adjusting either of jacket/wrap 11a or fastener 12a.

Jacket/wrap 11a is provided with pocket 13a. In one embodiment, pocket 13a is integral with jacket/wrap 11a. More specifically, jacket/wrap 11a is provided with a cavity (not illustrated in Figures) that can contain heating and/or cooling pack 14a. In another embodiment, pocket 13a is connected to jacket/wrap 11a. Pocket 13a can be permanently attached to jacket/wrap 11a and has an opening 13ai to receive heating pack and/or cooling pack 14a. Alternatively, pocket 14a can be attached to and detached from any portion of the jacket/wrap 11a such that heating and/or cooling pack 14a can be inserted through opening 13ai and positioned at desired location on desired body part of animal 05.

At least one of heating pack and/or cooling pack 14a is positioned in pocket 13a. In one embodiment, heating pack and cooling pack 14a is a pack of gel. Temperature of gel can be raised to use the pack as heating pack and temperature of gel can be lowered to use the pack as cooling pack. Alternatively, heating pack and cooling pack 14a is a pack of fluid that can be warm fluid, cold fluid or ice cubes. Heating pack and/or cooling pack 14a can be replaced with another heating pack and/or cooling pack 14a or can be refilled with another fluid/gel.

Referring now to the drawings, FIGS. 4-6, where the present invention is generally referred to with numeral 10b, it can be observed that a cylindrical-shaped therapeutic pad, in accordance with one embodiment, is provided that includes a jacket/wrap 11b, at least one fastener 12b, a pocket 13b and at least one of a heating pack and/or a cooling pack 14b.

As jacket/wrap 11b is cylindrical in shape, jacket/wrap 11b can be wearable on at least one of hand, legs, neck, tail and/or back portion(s) 05b of animal 05 such as a cat. As illustrated in FIG. 4, jacket/wrap 11b is wrapped around a portion of leg as well as back portion of cat. Jacket/wrap 11b can be typically of a material flexible enough to take the shape of the hand, legs, neck tail and/or back portion(s) 05b of animal 05. In one embodiment, jacket/wrap 11b can be made of stretchable material that can be stretched enough to be worn by animal 05 or can be provided with fastener 12b that can help jacket/wrap 11b to be worn by animal 05. Jacket/wrap 11b is adjustable such that it can be worn or wrapped on different body parts of animal 05 such as jacket/wrap 11b can be wrapped or worn on hands, legs, neck, tail or back portions by adjusting either of jacket/wrap 11b or fastener 12b. Material of jacket/wrap 11a can be selected such that the animal 05 is detoured from liking or chewing the wound on which jacket/wrap is worn or wrapped, thus preventing the need to use the cone of shame.

Fastener 12b, pocket 13b and heating pack and/or a cooling pack 14b is similar in construction and working to respective fastener 12a, pocket 13a and heating pack and/or a cooling pack 14a and hence not described for the sake of brevity.

Thus, therapeutic pad 10a and 10b provides treatment on any portion of body of animal 05 without restricting their mobility. Therapeutic pad 10a and 10b protects the wound or surgical stitch mark from being licked or chewed by animal using therapeutic pad 10a and 10b. Also, therapeutic pad 10a and 10b facilitated to heal the wound or surgical stitch mark or provide relief for pain which other is not experienced by use of surgical suits or cone of shame.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A therapeutic pad for an animal, said therapeutic pad consisting of:

a jacket/wrap wearable by the animal, wherein said jacket/wrap has an open configuration and a closed configuration, wherein said jacket/wrap has a top portion, a central portion and a bottom portion in said open configuration, wherein sides of said bottom portion and sides of said top portion are concave curved, wherein said top portion and said bottom portion are connected in said central portion, said central portion having a smaller length than the length in said bottom portion and said top portion, wherein the uppermost end of said top portion includes a first hook and loop member, said first hook and loop member extends horizontally in said uppermost end of said top portion, wherein the bottommost end of said bottom portion includes a second hook and loop member, said second hook and loop member extends horizontally and fully covering said bottommost end of said bottom portion, wherein said first hook and loop member and said second hook and loop member are engaged together defining said closed configuration, wherein said central portion is configured to be placed in the back of said animal, wherein said first hook and loop member and said second hook and loop member are configured to engage together in an abdomen of said animal, being diametrically opposite to said central portion;

a pocket defined to be integral with or connected with said jacket/wrap, wherein in said open configuration said pocket is horizontally aligned in said central portion; and a heating pack and a cooling pack positioned in said pocket, wherein said pocket is attached with and detached from desired portions of said jacket/wrap and has an opening to receive and remove said heating pack and said cooling pack, wherein said pocket is a cavity formed within said jacket/wrap to house said heating pack and said cooling pack, wherein said heating pack is filled with gel or hot/warm fluid, wherein said cooling pack is a gel or refillable cold/cool fluid, wherein said heating pack and said cooling pack are refillable or replaceable.

* * * * *